United States Patent [19]
Arnold et al.

[11] Patent Number: 5,724,984
[45] Date of Patent: Mar. 10, 1998

[54] MULTI-SEGMENT ECG ELECTRODE AND SYSTEM

[75] Inventors: Jeffrey M. Arnold, Wellesley; Paul Albrecht, Bedford; Richard J. Cohen, Waban, all of Mass.; Harvey Levin, Chester, N.H.

[73] Assignee: Cambridge Heart, Inc., Bedford, Mass.

[21] Appl. No.: 682,076

[22] Filed: Jul. 17, 1996

Related U.S. Application Data

[63] Continuation-in-part of Ser. No. 379,375, Jan. 26, 1995, and a continuation-in-part of Ser. No. 557,883, Nov. 14, 1995, and a continuation-in-part of Ser. No. 665,434, Jun. 18, 1996, abandoned.

[51] Int. Cl.$^6$ .................................................. A61B 5/0408
[52] U.S. Cl. .................................................. 128/696; 128/640
[58] Field of Search .................................. 128/696, 698, 128/639–641, 644; 607/148, 149, 152

[56] References Cited

U.S. PATENT DOCUMENTS

| | | |
|---|---|---|
| 3,868,947 | 3/1975 | Holsinger . |
| 4,082,087 | 4/1978 | Howson ................................. 128/640 |
| 4,084,583 | 4/1978 | Hjort . |
| 4,362,164 | 12/1982 | Little et al. ............................ 128/639 |
| 4,362,165 | 12/1982 | Carmon et al. ....................... 128/640 |
| 4,365,634 | 12/1982 | Bare et al. ............................ 128/640 |
| 4,421,121 | 12/1983 | Whisler et al. ....................... 128/731 |
| 4,422,459 | 12/1983 | Simson ................................. 128/702 |
| 4,448,199 | 5/1984 | Schmid ................................. 128/639 |
| 4,583,549 | 4/1986 | Manoli ................................. 128/640 |
| 4,583,551 | 4/1986 | Pike ..................................... 128/640 |
| 4,630,204 | 12/1986 | Mortara ................................ 364/417 |
| 4,763,660 | 8/1988 | Kroll et al. ........................... 128/640 |
| 4,951,672 | 8/1990 | Buchwald et al. ................... 128/653 SC |
| 4,955,381 | 9/1990 | Way et al. ............................ 128/640 |
| 4,955,383 | 9/1990 | Faupel ................................. 128/639 |
| 4,979,110 | 12/1990 | Albrecht et al. . |
| 5,184,620 | 2/1993 | Cudahy et al. ....................... 128/639 |
| 5,224,479 | 7/1993 | Sekine ................................. 128/644 |
| 5,295,482 | 3/1994 | Clare et al. .......................... 128/639 |
| 5,305,746 | 4/1994 | Fendrock ............................. 128/641 |
| 5,366,497 | 11/1994 | Ilvento et al. ........................ 607/142 |
| 5,507,290 | 4/1996 | Kelly et al. .......................... 128/640 |
| 5,520,683 | 5/1996 | Subramaniam et al. ............. 607/152 X |

FOREIGN PATENT DOCUMENTS 9119531 12/1991 WIPO ....................................... 128/639

OTHER PUBLICATIONS

Kaufer et al., "Optimization of Multi–Ring Sensing Electrode Set," Annual International Conference of the IEEE Engineering in Medicine and Biology Society, vol. 12, No. 2, pp. 0612–0613 (1990).

Kaufer et al., "In Vivo Detection and Classification of Cardiac Rhythms Using Concentric Ring Electrodes," IEEE Engineering in Medicine and Biology Society, vol. 13, No. 2, p. 0722 (1991).

Primary Examiner—Jeffrey R. Jastrzab
Attorney, Agent, or Firm—Fish & Richardson P.C.

[57] ABSTRACT

A multi-segment ECG electrode includes a flexible basepad, a central segment defined on a surface of the basepad, and exterior segments defined on the surface of the basepad. The exterior segments may be sized, shaped and positioned relative to the central segment so that an average position of the exterior segments approximates a position of the central segment.

30 Claims, 4 Drawing Sheets

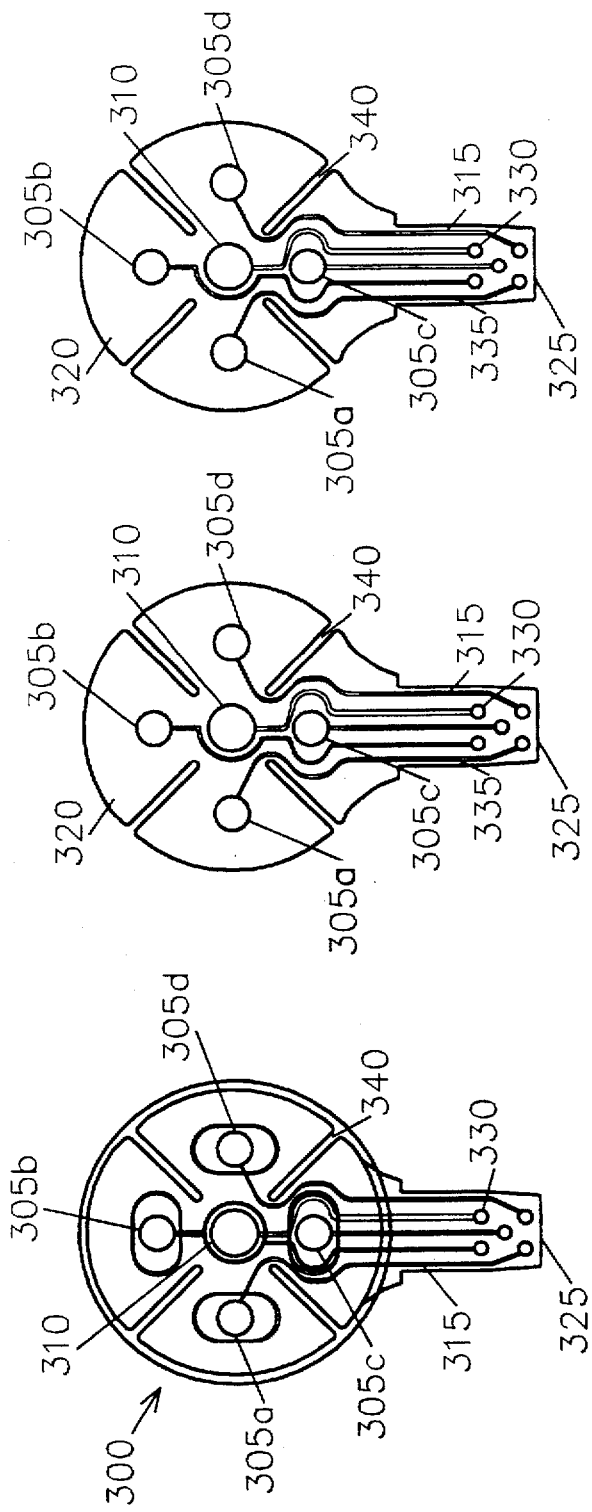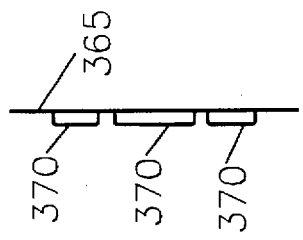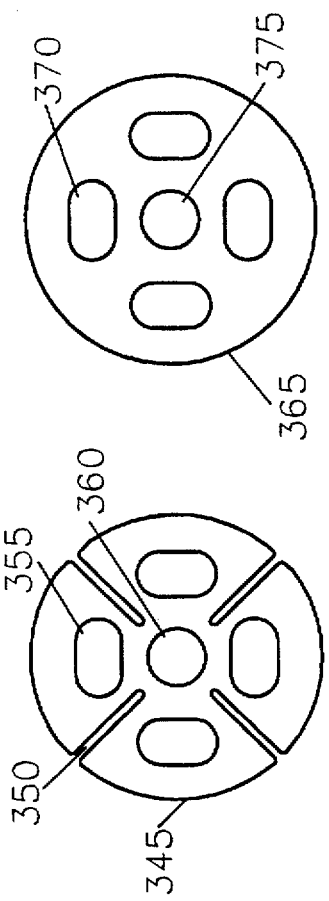

5,724,984

1

MULTI-SEGMENT ECG ELECTRODE AND SYSTEM

CROSS REFERENCE TO RELATED APPLICATIONS

This application is a continuation-in-part of U.S. application Ser. No. 08/379,375, filed Jan. 26, 1995 and entitled "Measuring and Assessing Cardiac Electrical Stability"; U.S. application Ser. No. 08/557,883, filed Nov. 14, 1995 and entitled "Using Related Signals to Reduce ECG Noise"; and U.S. application Ser. No. 08/665,434, filed Jun. 18, 1996 and entitled "Electrode Connector" now abandoned. These applications are incorporated herein by reference.

BACKGROUND OF THE INVENTION

The invention relates to electrocardiogram (ECG) electrodes.

Many medical systems, such as ECG systems, use electrodes to obtain signals from a patient. The physiologic signal underlying an ECG waveform may be obtained through electrodes attached to a patient's chest. Typically, each electrode includes a terminal that may be connected electrically to a lead of the ECG system and an adhesive portion that may be attached to the patient's skin. A layer of electrically conductive gel provides a conduction path between the terminal and the patient's skin. The gel contacts the patient's skin and detects electrical signals produced by the patient's heart. The detected signals are then transmitted, via the terminal and the lead, to ECG circuitry for processing and display.

SUMMARY OF THE INVENTION

The invention is directed to an ECG electrode that includes multiple terminals, each of which corresponds to an electrode segment. For purposes of the invention, a segment is defined as a conductive area on an electrode that is intended to make electrical contact with a patient, and that does not completely surround another segment. Thus, for example, a ring electrode is not a segment. Two or more exterior segments of the multi-segment electrode are positioned around a central segment of the electrode. The exterior segments may be shaped, sized, and positioned so that an average of the positions of the exterior segments approximates the position of the central segment.

Multi-segment electrodes may be used in producing low-noise ECG signals. A major source of noise in ECG signals is baseline noise generated in the electrode. The baseline noise is low frequency noise that appears as an undulating baseline upon which the ECG rides. Baseline noise is attributable to motion and deformation of the electrode and its associated gel, and results from low frequency events such as patient respiration and patient motion. As a result, the magnitude of baseline noise tends to increase with exercise. However, many important ECG measurements must be made during exercise.

Noise reduction is of particular importance in applications that attempt to measure low level ECG features such as ST segment changes, P waves, or the fetal ECG, and of even more importance in applications that attempt to measure microvolt level features of the ECG, such as electrical alternans, late potentials such as might be measured by a signal averaged ECG (SAECG), or His-Purkinje activity. For example, alternans, a subtle beat-to-beat change in the repeating pattern of an ECG waveform, can be indicative of electrical instability of the heart and increased susceptibility to sudden cardiac death. Noise in the ECG waveform can mask the presence of alternans. The noise also can mimic the presence of alternans when there is none.

Techniques for using multi-segment electrodes to reduce noise in ECG signals are discussed in U.S. application Ser. No. 08/379,375, filed Jan. 26, 1995 and entitled "Measuring and Assessing Cardiac Electrical Stability" and U.S. application Ser. No. 08/557,883, filed Nov. 14, 1995 and entitled "Using Related Signals to Reduce ECG Noise".

In one aspect, generally, the invention features a multi-segment ECG electrode. The electrode includes a flexible basepad and a central segment defined on a surface of the basepad. Exterior segments are defined on the surface of the basepad and positioned around the central segment.

Embodiments of the invention may include one or more of the following features. An average position of the exterior segments may approximate a position of the central segment. The basepad may include a narrow region that defines a connection tail, and conductive traces may extend from each of the segments to the connection tail. One or more holes may extend through the connection tails. The holes also may extend through the conductive traces so that the holes provide regions at which conductive elements of a connector may make electrical contact with the conductive traces.

A layer of flexible, insulating foam may be positioned on the surface of the flexible base pad and on the conductive traces. The foam may include cutouts that form wells corresponding to the positions of the central segment and the exterior segments. The wells may be filled with conductive gel. The foam also may include an adhesive layer for attachment to a patient's skin.

The segments may be formed by printing with a conductive material on the surface of the flexible base pad. The conductive material may be, for example, silver-chloride ink.

The exterior segments may define a broken ring around the central segment. The central segment may have a circular shape, and the exterior segments may have arcuate shapes. The electrode may include only three exterior segments that together define the broken ring.

The multi-segment ECG electrode may be included in an electrocardiogram system. The electrode may be configured for attachment to a patient's skin to detect electrical signals produced by the patient. The system also may include a processor and a lead connected between the multi-segment ECG electrode and the processor to deliver electrical signals detected by the multi-segment ECG electrode to the processor. The processor may be configured to process the electrical signals to detect alternans. Similarly, the processor may be configured to process the electrical signals to detect a fetal ECG signal, or to perform any of the other measurement applications noted above.

The multi-segment ECG electrode may be configured for use with a connector that includes a connector housing, conductive contacts positioned in the connector housing and having tapered ends, a seating surface positioned in the connector housing opposite the tapered ends of the conductive contacts, the seating surface and the tapered ends of the contacts being configured to positively retain the multi-segment ECG electrode when connection holes of the multi-segment ECG electrode are positioned around the tapered end of the conductive contacts, and a mechanism for pressing the seating surface against the tapered ends of the conductive contacts. In this regard, the multi-segment ECG electrode may include connection holes formed in the basepad. The connection holes may be sized to be larger than a first portion of the tapered end of a conductive contact and smaller than a second portion of the tapered end of the conductive contact. Conductive paths may be formed on the basepad from each of the segments to regions surrounding corresponding connection holes. The basepad of the multi-segment ECG electrode may be configured to be deformed by pressure applied by the seating surface and the mechanism in regions surrounding the connection holes.

Other features and advantages of the invention will become apparent from the following description of the preferred embodiment, including the drawings, and from the claims.

BRIEF DESCRIPTION OF THE DRAWINGS

FIG. 9A is a top view of an electrode.

FIGS. 9B and 9C are top views of a basepad of the electrode of FIG. 9A.

FIG. 9D is a top view of a foam pad of the electrode of FIG. 9A.

FIGS. 9E and 9F are top and side views of a cover of the electrode of FIG. 9A.

DESCRIPTION OF THE PREFERRED EMBODIMENT

Figure 1:
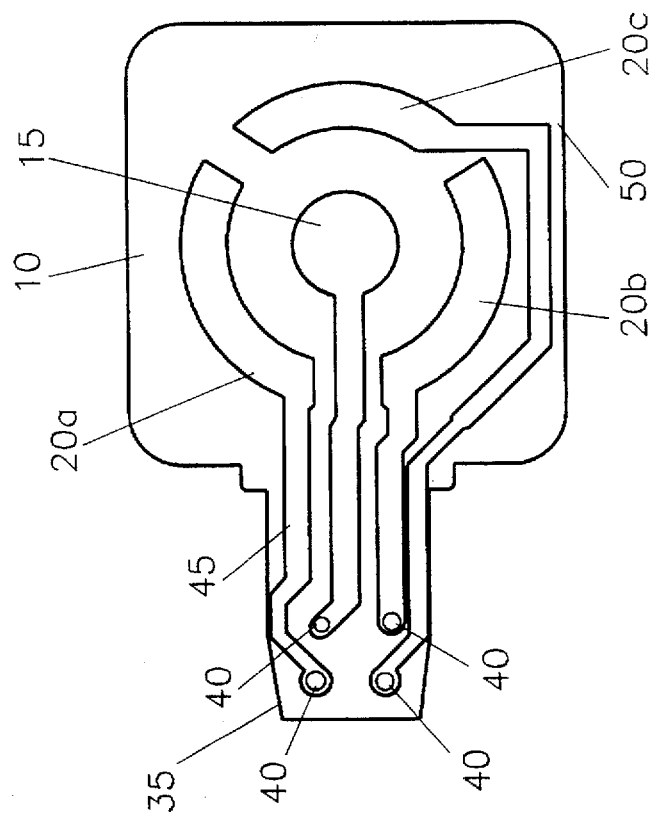
FIG. 1 is a top view of an electrode and a connector assembly.
Figure 1:
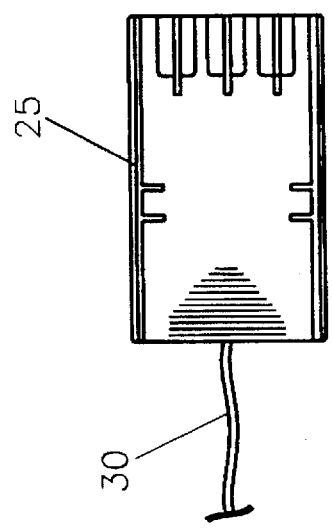

Referring to FIG. 1, a multi-segment electrode 10 includes a center segment 15 and three arcuate exterior segments 20a, 20b and 20c that together surround the center segment 15. The position of the center segment 15 corresponds to the average of the positions of the arcuate segments 20a, 20b, 20c.

The multi-segment electrode 10 is configured for use with a connector 25 that is attached to a lead 30. To this end, the electrode 10 includes a connection tail 35. The connection tail 35 includes four connection holes 40 for attachment to the connector 25. The connection holes 40 are arranged in a square configuration. Each hole 40 passes through an extension 45, or trace, of a segment of the electrode 10. The construction and operation of the connector 25 is discussed in detail in U.S. application Ser. No. 08/665,434, filed Jun. 18, 1996 and entitled "Electrode Connector" now abandoned.

Figure 2:
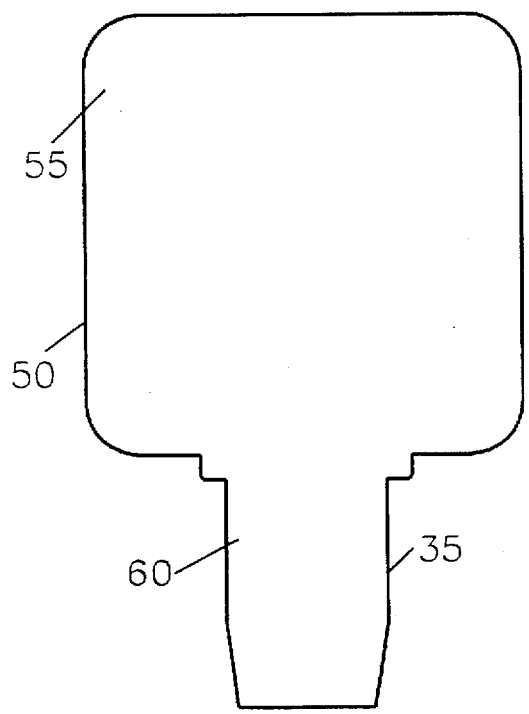
FIGS. 2–5 are bottom views of the electrode of FIG. 1 during different stages of construction of that electrode.

Referring to FIG. 2, the multi-segment electrode 10 is formed on a basepad 50. The basepad is made from an insulating, flexible film, such as polyester film. The basepad 50 is shaped to include a section 55 corresponding to the body of the electrode and a section 60 corresponding to the connection tail 35.

Figure 3:
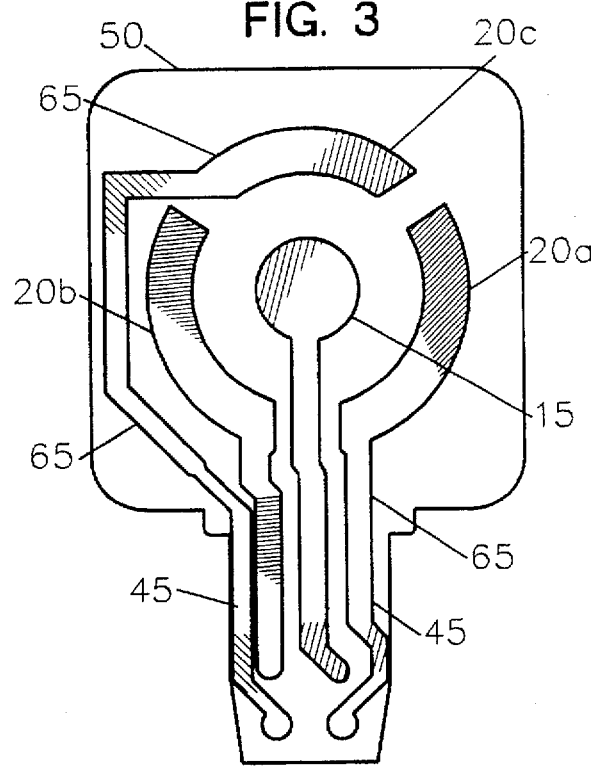
Figure 4:
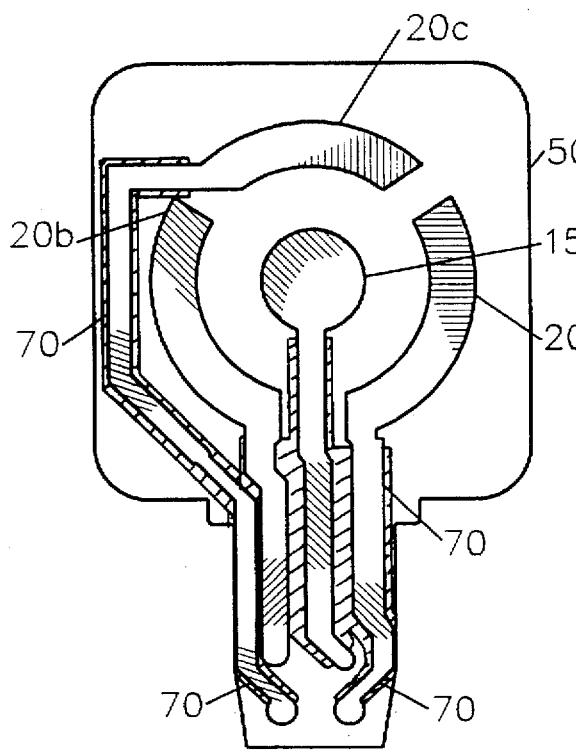

As shown in FIG. 3, the segments 15, 20a, 20b and 20c are formed by printing on the surface of the basepad 50 with a conductive material 65, such as silver-chloride ink. The extensions 45 are formed in the same manner. Next, as shown in FIG. 4, a layer of insulating material 70 is deposited on the silver-chloride ink 65 that defines the extensions 45. With the exception of portions of the extensions that will be adjacent to the holes 40, the insulating material covers the entire surface area of the extensions.

Figure 5:
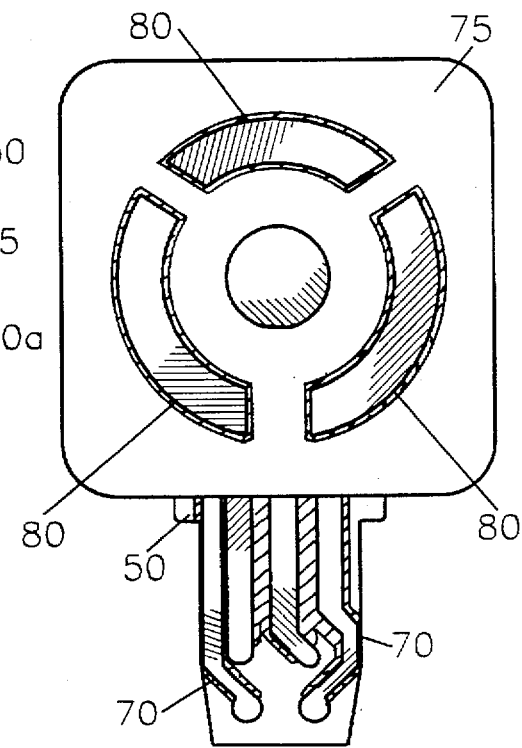
Figure 6:
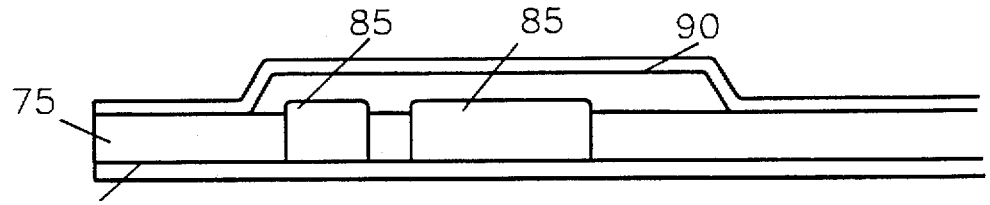
FIG. 6 is a side view of the electrode of FIG. 1.

Referring to FIG. 5, a layer of plastic flexible foam 75 is attached to the section 55 of the basepad 50 corresponding to the body of the electrode. The foam is positioned on top of the silver-chloride ink 65 and the insulating material 70 so that the ink and the insulating material are sandwiched between the foam and the basepad. The foam includes cutout sections 80 that correspond to the electrode segments 15, 20a, 20b and 20c. The cutout sections form wells that hold electrically conductive gel 85 (FIG. 6). The gel 85 provides a conductive path from the patient's skin to the silver-chloride ink that defines each electrode segment.

The holes 40 are formed through the basepad 50 and the silver-chloride ink to produce the electrode 10 illustrated in FIG. 1. Referring to FIG. 6, in storage and prior to use, a cover 90 is attached to the adhesive surface of the foam 75 to keep the electrode clean prior to use and to prevent the conductive gel 85 from drying.

Use of the three exterior segments 20a, 20b and 20c provides advantages over the use of a continuous ring electrode surrounding the center segment 15. In particular, it is often desirable to measure the average voltage underlying the ring defined by the segments 20a, 20b, 20c. If a continuous ring were used, and the skin were inconsistently conductive, then the resulting signal would be a weighted average of the voltages underlying the ring, with a heavier weight being applied to regions of high conductivity. By separating the ring into multiple segments and electronically buffering and adding the contribution of each ring segment, the multi-segment electrode 10 prevents one segment of the ring from dominating an average voltage signal produced for the ring.

Figure 7:
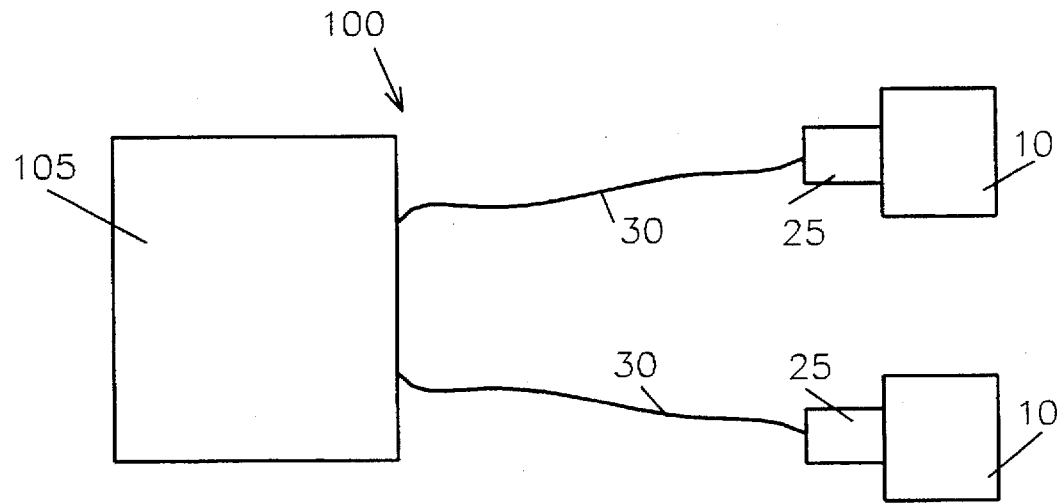
FIG. 7 is a block diagram of an electrocardiogram system.

Referring to FIG. 7, one or more electrodes 10 may be included in an electrocardiogram (ECG) system 100 that also includes a processor 105. The electrodes 10 are attached to a patient's skin and positioned to detect electrical signals produced by the patient's heart.

The processor 105 may be configured to detect alternans, a subtle beat-to-beat change in the repeating pattern of an ECG waveform, which can be indicative of electrical instability of the heart and increased susceptibility to sudden cardiac death. ECG systems configured to detect alternans are discussed in U.S. application Ser. No. 08/379,375, filed Jan. 26, 1995 and entitled "Measuring and Assessing Cardiac Electrical Stability", and U.S. application Ser. No. 08/557,883, filed Nov. 14, 1995, and entitled "Using Related Signals to Reduce ECG Noise".

The processor 105 may be further configured to detect ECG P-waves. The P-wave is a portion of an ECG signal that results from activity in the atrium of the heart. An improved representation of the P-wave may be obtained by monitoring a multi-segment electrode positioned in a region that overlies the atrium.

Similarly, the processor 105 may be configured to monitor the fetal ECG. When the processor 105 is so configured, a multi-segment electrode is placed on a patient's abdomen in a region overlying the expected position of the fetus, and the processor 105 monitors the signals produced by the electrode.

Figure 8:
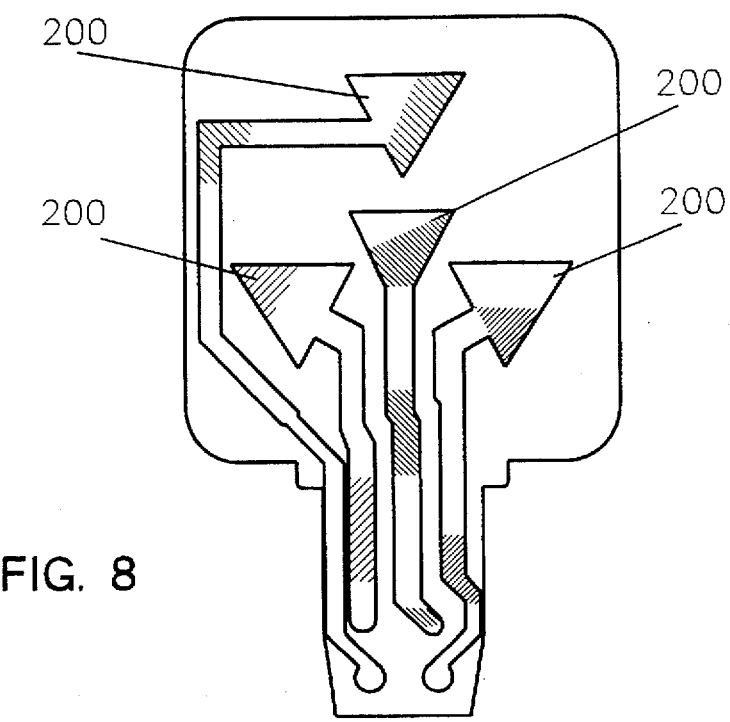
FIG. 8 is a top view of an electrode.

Other embodiments are within the following claims. For example, the circular segment 15 and the arcuate segments 20a, 20b, 20c could be replaced with the triangular segments 200 illustrated in FIG. 8. Similarly, the radial spacing from the center segment could vary for different ones of the exterior segments. In addition, the center segment could be divided into multiple segments.

Also, the number of exterior segments could be increased. For example, the electrode 300 illustrated in FIGS. 9A–9F includes four oval exterior segments 305a, 305b, 305c, and 305d that surround a circular center segment 310.

As with the electrode 10, the segments 305, 310 and traces 315 of the electrode 300 are formed on a flexible basepad 320 by printing with conductive silver/silver chloride ink (FIG. 9B). As formed on the basepad 320, the segments 305 have circular shapes. The traces 315 extend to a connection tail 325 of the basepad. Holes 330 are formed in the connection tail 325 at the end of each trace 315. The traces 315 are covered with an insulating material 335 (FIG. 9C).

Cutouts 340 are positioned around the outer perimeter of the basepad to provide added flexibility and resistance to buckling. The cutouts are positioned to define four regions that each include a segment 305.

A layer of flexible foam 345 (FIG. 9D) is positioned on top of the basepad 320. The outer periphery of the foam 345 includes cutouts 350 in positions corresponding to the positions of the cutouts 340 in the basepad 320. The foam also includes cutouts 355 and 360 that correspond, respectively, to the positions of the segments 305 and 310. The cutouts 355 have generally oval shapes and are filled with conductive gel.

A transparent cover 365 (FIGS. 9E and 9F) is positioned over the foam 345 for storage and prior to use. The cover 365 includes raised regions 370 and 375 that correspond, respectively, to the segments 305 and 310.

What is claimed is:

1. A multi-segment ECG electrode, comprising:
a flexible basepad,
a central conductive segment defined on the basepad,
exterior conductive segments defined on the basepad and positioned around the central segment, and
conductive traces extending from the central conductive segment and from each of the exterior conductive segments to a common region of the basepad,
wherein:
an average position of the exterior segments corresponds to a position of the central segment,
the basepad further comprises a connection tail,
the common region of the basepad is located at the connection tail, and
a hole extends through the connection tail.

2. The multi-segment ECG electrode of claim 1, wherein the hole extends through one of the conductive traces.

3. The multi-segment ECG electrode of claim 1, further comprising a layer of flexible, insulating foam positioned on the surface of the flexible basepad and on the conductive traces.

4. The multi-segment ECG electrode of claim 3, wherein the foam includes cutouts that form wells corresponding to the positions of the central segment and the exterior segments.

5. The multi-segment ECG electrode of claim 4, wherein the wells are filled with conductive gel.

6. The multi-segment ECG electrode of claim 3, wherein the foam includes an adhesive layer for attachment to a patient's skin.

7. The multi-segment ECG electrode of claim 1, wherein the central segment and the exterior segments are formed by printing with a conductive material on the surface of the flexible base pad.

8. The multi-segment ECG electrode of claim 7, wherein the conductive material is silver-chloride ink.

9. The multi-segment ECG electrode of claim 1, wherein the exterior segments define a broken ring around the central segment.

10. The multi-segment ECG electrode of claim 9, wherein the central segment has a circular shape.

11. The multi-segment ECG electrode of claim 9, wherein the exterior segments have arcuate shapes.

12. The multi-segment ECG electrode of claim 9, wherein the electrode includes only three exterior segments that together define the broken ring.

13. The multi-segment ECG electrode of claim 12, wherein the exterior segments have arcuate shapes.

14. The multi-segment ECG electrode of claim 1, wherein the flexible basepad includes cutouts that provide increased flexibility.

15. The multi-segment ECG electrode of claim 14, wherein an outer periphery of the flexible basepad includes the cutouts that provide increased flexibility.

16. An electrocardiogram system including the multi-segment ECG electrode of claim 1, wherein the multi-segment ECG electrode is configured for attachment to a patient's skin to detect electrical signals produced by the patient and the system further comprises:
a processor configured to generate an ECG waveform based on electrical signals detected by the multi-segment ECG electrode;
a lead connected between the multi-segment ECG electrode and the processor to deliver the electrical signals detected by the multi-segment ECG electrode to the processor; and
a display connected to the processor and configured to display the ECG waveform.

17. The electrocardiogram system of claim 16, wherein the processor is configured to process the electrical signals to detect alternans.

18. The electrocardiogram system of claim 16, wherein the processor is configured to process the electrical signals to detect a fetal ECG signal.

19. The electrocardiogram system of claim 16, wherein the processor is configured to process the electrical signals to detect ECG P waves.

20. A multi-segment ECG electrode, comprising:
a flexible basepad,
a central conductive segment defined on the basepad,
exterior conductive segments defined on the basepad and positioned around the central segment, and
conductive traces extending from the central conductive segment and from each of the exterior conductive segments to a common region of the basepad,
wherein:
the basepad further comprises a connection tail,
the common region of the basepad is located at the connection tail,
holes extend through the connection tail, and
each conductive trace is positioned on a region of the connection tail through which a hole extends.

21. A multi-segment ECG electrode, comprising:
a flexible basepad,
a central conductive segment defined on the basepad, and
exterior conductive segments defined on the basepad and positioned around the central segment,
wherein the multi-segment ECG electrode is configured for use with a connector that includes a connector housing, a conductive contact positioned in the connector housing and having a tapered end, and a seating surface positioned in the connector housing opposite the tapered end of the conductive contact, the multi-segment ECG electrode further comprising:

a connection hole formed in the basepad, the connection hole being sized to be larger than a first portion of the tapered end of the conductive contact and smaller than a second portion of the tapered end of the conductive contact, and a conductive path formed on the basepad from one of the exterior segments to a region surrounding the connection hole.

22. The multi-segment ECG electrode of claim 21, wherein the basepad is configured to be deformed by pressure applied by the seating surface and the mechanism in a region surrounding the connection hole.

23. The multi-segment ECG electrode of claim 21, wherein the multi-segment ECG electrode further comprises:

multiple connection holes formed in the basepad; and conductive paths formed on the basepad from each of the segments to regions surrounding corresponding connection holes.

24. A multi-segment ECG electrode, comprising:

a flexible basepad, a central conductive segment defined on the basepad, exterior conductive segments defined on the basepad and positioned around the central segment, and a conductive trace extending from the central segment and each of the exterior segments, wherein:

the basepad further comprises a connection tail, the conductive traces extend to the connection tail, and a hole extends through the connection tail.

25. The multi-segment ECG electrode of claim 24, wherein the hole extends through one of the conductive traces.

26. The multi-segment ECG electrode of claim 24, wherein each conductive trace is positioned on a region of the connection tail through which a hole extends.

27. The multi-segment ECG electrode of claim 24, wherein the exterior segments define a broken ring around the central segment.

28. The multi-segment ECG electrode of claim 27, wherein the electrode includes only three exterior segments that together define the broken ring.

29. The multi-segment ECG electrode of claim 24, wherein the flexible basepad includes cutouts that provide increased flexibility.

30. The multi-segment ECG electrode of claim 29, wherein an outer periphery of the flexible basepad includes the cutouts that provide increased flexibility.

* * * * *